United States Patent [19]

Honigs et al.

[11] Patent Number: 5,251,006
[45] Date of Patent: Oct. 5, 1993

[54] AUTOMATIC SPECTROPHOTOMETER CALIBRATION SYSTEM

[75] Inventors: David E. Honigs, Laurel; Timothy G. Kelly, Silver Spring, both of Md.

[73] Assignee: NIRSystems Incorporated, Silver Spring, Md.

[21] Appl. No.: 666,139

[22] Filed: Mar. 7, 1991

[51] Int. Cl.⁵ .................. G01J 3/06; G01J 3/18
[52] U.S. Cl. ......................... 356/319; 356/308
[58] Field of Search ............ 356/305, 308, 328, 319, 356/331–334; 250/252.1 A

[56] References Cited

U.S. PATENT DOCUMENTS

| | | | |
|---|---|---|---|
| 4,969,739 | 11/1990 | McGee | 356/308 |
| 4,971,439 | 11/1990 | Brown | 356/334 |
| 4,997,280 | 3/1991 | Norris | 356/308 |
| 5,020,909 | 6/1991 | Landa | 356/300 |

FOREIGN PATENT DOCUMENTS

378108A2  7/1990 European Pat. Off. .
381053    8/1990 European Pat. Off. .
2135770   9/1984 United Kingdom .

Primary Examiner—Vincent P. McGraw
Assistant Examiner—K. P. Hantis
Attorney, Agent, or Firm—Lane, Aitken & McCann

[57] ABSTRACT

In a spectrophotometer having an oscillating grating, an automatic calibration system is provided to ensure that the instrument constants are recomputed before each measurement of an unknown sample. In the system, whenever a reference scan is carried out, a second scan through an absorbance standard is carried out automatically and the data obtained is used to correct the instrument coefficients relating the angular position of the grating to the wavelength. The corrected coefficients are then stored to be used in the measurement of the unknown sample immediately thereafter. For near infrared spectrum measurements, the absorbance standard is a polystyrene plate. For visual measurements, the absorbance standard is a didymium plate. The didymium plate is mounted on the polystyrene plates eclipse a portion of the polystyrene plate.

7 Claims, 3 Drawing Sheets

ABSORBANCE V.S. WAVELENGTH – SAMPLE SCAN

AUTOMATIC SPECTROPHOTOMETER CALIBRATION SYSTEM

BACKGROUND OF THE INVENTION

This invention relates to a method and apparatus designed to automatically calibrate a spectrophotometer. Spectrophotometers are optical instruments employed for both the qualitative and quantitative analysis of a variety of materials. Samples having unknown constituents are analyzed by sequentially illuminating a sample with narrow wavelength bands across the spectrum of an elected range of electromagnetic radiation and then measuring the intensity of light transmitted or reflected from the sample. Light can be dispersed into its constituent band wavelengths by a grating or a conventional prism. In spectrophotometers, gratings are employed because of their ability to disperse light into narrow wavelength bands so that the light in the bands is close to being monochromatic. The grating is oscillated with respect to the light source so that light reflected from the grating passes through a narrow slit. The light exiting the slit is restricted to a narrow wavelength band which is scanned through a wavelength range of the desired region of the spectrum. Light passing through the exit slit is directed to a sample to be analyzed and photodetectors measure the light either reflected or transmitted by the sample. Near infrared spectrophotometry, involving the use of electromagnetic radiation of wavelengths between 1100 Angstrom and 2500 Angstrom, is a particularly effective tool in the analysis of organic compounds because of their significant exhibition of absorptive characteristics in the near infrared region of the spectrum.

Although the spectrophotometers as described above are effective at measuring absorptive properties of materials, it has been difficult to maintain precise calibration of the instruments to ensure accuracy of the absorbance measurements. These problems are manifested as variations in the precise wavelength that pass through the exit slit at a given angular position of the grating with respect to the light source. The center wavelength passing through the exit is related to the angular position by a trigonometric expression which has constants that are unique to each instrument. However, the constants are subject to variations with temperature and drift with time. As a result, the constants of the instrument can change with each measurement and measurements taken with the instruments lose precision and are not precisely repeatable.

In order to compensate for the variations in the instruments, the spectrophotometers are routinely calibrated. In the past, one method of calibration was performed by inserting a standard, such as polystyrene, into the path of light exiting the housing of the spectrophotometer which contained the grating. The standard selected had peaks of absorbance occurring at precisely known wavelengths. By determining the angular positions of the grating where the known peaks occur, the coefficients for the instruments could be calculated and then entered into the instrument's computer. Coefficients entered into the computer would remain unchanged until it was determined that the instrument should be recalibrated. Often the determination that an instrument should be recalibrated was not made frequently enough to maintain the precision of the measurements up to the instrument capability. The present invention increases the precision and reliability of each instrument by automatically recalibrating the instrument before each measurement of an unknown sample in a manner invisible to the user. Thus, the present invention provides an apparatus providing more accurate measurements.

SUMMARY OF THE INVENTION

The automatic calibration apparatus according to the invention is designed to be employed in a conventional spectrophotometer such as those disclosed in the Landa U.S. Pat. No. 4,264,205 or McGee U.S. Pat. No. 4,969,739. Central to the invention, is the integration of permanent reference standards in the spectrophotometer from which the spectrophotometers are calibrated. The reference standards are mounted on a pivoting paddle controlled by a stepper motor which automatically positions the paddles into the path of light dispersed by the grating. The present invention employs polystyrene and didymium plates located within the confines of the housing which contains the reflecting grating. When the operator desires to make a measurement of an unknown sample, the following sequence of events is initiated. First, the operator selects the region of the spectrum to be scanned, either infrared or visible. Then, a computer screen displays a prompt to the operator to make a reference scan. In response to the prompt, the operator actuates an instrument key to effect the reference scan. In response to the key actuation, the wavelength output from the spectrophotometer is scanned through the spectrum without an absorbing sample in the light path. Measuring of the intensity of light either reflected or transmitted are made throughout the spectrum. A stepper motor then pivots a paddle carrying an absorbance standard into the path of the dispersed light directed towards the exit slit of the housing, and the wavelength output from the spectrophotometer is again scanned through the spectrum. Measurements of the intensity of light reflected or transmitted are again taken throughout the spectrum. Data generated from a scan of the absorbance standard is expressed as a curve having peaks which represent absorbance. The position of the peaks which correspond to a certain wavelength are compared with the wavelengths where the absorbance peaks are known to occur for the respective standards. From this data, using linear regression, the coefficients for the spectrophotometer are adjusted and the adjusted coefficients are stored in the computer memory. Immediately following the above-described reference scan procedure, the instrument can measure either the reflectance or transmittance of the unknown sample through the spectrum and the updated coefficients are used to relate the shaft angular position to the wavelength. Thus, the reflectance or transmittance of the unknown samples can be determined at precisely known wavelengths.

The present invention can be used in either the infrared or visible light spectrum. If it is desired to employ the spectrophotometer in the infrared light region of the spectrum, a polystyrene plate is used as the absorbance standard. If the operator desires to measure in the visible range, a didymium plate is used as the absorbance standard.

DETAILED DESCRIPTION OF THE INVENTION

Figure 1:
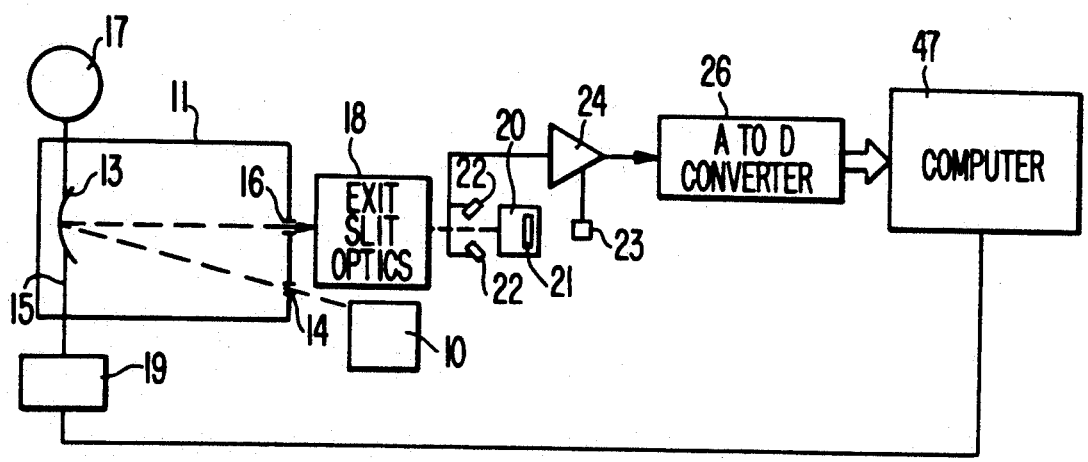
FIG. 1. is a schematic of a spectrophotometer according to the invention.

As shown in FIG. 1 the spectrophotometer according to the present invention employs a source 10 of broad band radiation, which radiates both visible and near infrared light through the spectrum from 400 nanometers to 2500 nanometers. The radiation from the source 10 passes through an entrance slit 14 of a housing 11 to irradiate an optical grating 13. The grating 13 reflects and disperses the incident radiation into a spectrum. A motor 17 oscillates the grating at a rapid frequency, preferably greater than 0.5 cycles per second, but in no event less than 0.1 cycles per second. A shaft encoder 19, which is coupled to the shaft on which the grating oscillates, continuously measures the angular position of the shaft and digitally signals the angular position of the grating to a computer 47. The encoder generates a signal relating to the angular position of the shaft in increments of 0.025 degrees. An exit slit 16 allows a narrow wavelength band of the spectrum to pass out of the housing and, as the grating oscillates, the center wavelength of the narrow wavelength band is scanned through the spectrum.

Figure 2:
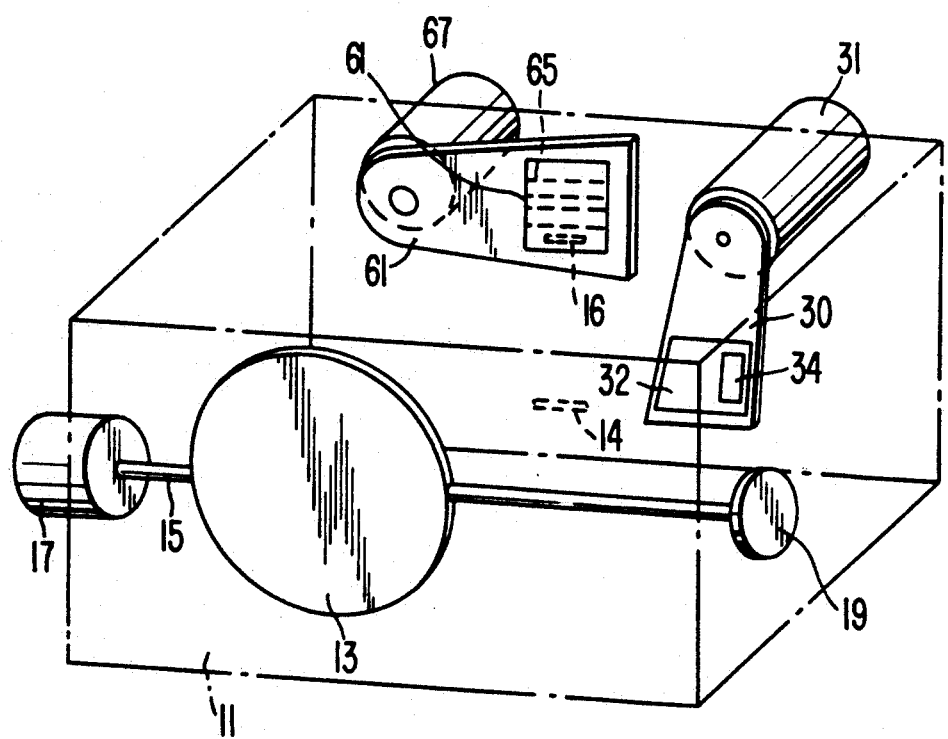
FIG. 2. is a perspective view of the spectrophotometer employed in the instrument of the invention.

As shown in FIG. 2, a paddle 30 is mounted in the housing 11 by a stepper motor 31. The stepper motor 31 is located on the housing 11 near the exit slit 16 and the paddle 30 is mounted on the drive shaft which extends into the housing 11. Adjacent to paddle 30 is a second paddle 61 also mounted for pivoting by a stepper motor 67. The first paddle 30 holds a polystyrene plate 32 and a didymium glass plate 34 which eclipses a portion of the polystyrene plate. The polystyrene and didymium plates are the permanent absorbance standards employed by the instrument. The stepper motor can pivot paddle 30 to either position the polystyrene plate into a path of the light exiting the housing or pivot the portion of the paddle with both the polystyrene and didymium plates into the path of the light. The polystyrene plate 32 transmits infrared light throughout the infrared range, and at known wavelengths exhibits absorbance by peaks in the curve for the measurements in the infrared spectrum.

In an alternative configuration designed to calibrate the instrument when operated in the visible light spectrum, the stepper motor positions the portion of the paddle with both the polystyrene and didymium plate within the path of light. While the polystyrene plate has only a slight effect on light in the visible range, didymium exhibits strong absorptive characteristics at specific wavelengths.

The light passing through the exit slit also passes through a filter plate 63 or 65, which removes higher order visible or near infrared wavelengths from the light beam. The filter plates 63 and 65 are mounted on the second paddle 61, which is positioned by stepper motor 67. Pivoting this paddle aligns the infrared transmitting filter 63 or the visible transmitting filter 65 in the path of the exiting light beam. The stepper motor 67 positions the paddle 61 in synchronism with the grating 13 as it oscillates to move the different transmitting filter segments into alignment with the exit slit 16 in order to limit the transmission through the exit slit to a single order of the dispersed light as described in U.S. Pat. No. 4,969,739.

After passing through filter 63 or 65, the light exits the housing 11 of the spectrophotometer. As shown in FIG. 1, the light passing through exit slit 16 is directed toward a sample holder 20 which can accept an unknown sample. Positioned adjacent to sample holder 20 are photodetectors 22 which measure the intensity of light reflected from the sample and photodetector 23, which is positioned to measure light intensity transmitted through the sample. Both reflectance and transmission are functions of the absorptive properties of a sample and provide characteristic data for analyzing a sample. The transmittance of a sample is determined by the following equation:

$$T = I/I_o$$

where T is the transmittance, $I_o$ is the intensity of the incident light and I is the intensity of the light transmitted through the sample. The intensity of the incident light is simply a measurement taken without a sample in the chamber. Similarly, the reflectance of a sample is determined by the equation:

$$R = I/I_o$$

in which $I_o$ is the intensity of the incident light and I is the intensity of the reflected light. To determine a measurement of $I_o$ for reflectance, a ceramic white diffusely reflecting plate is positioned in the sample chamber 20 and a reference scan is performed. The ceramic plate, which is available from the Coors Corporation, has very little signature absorbance through the near infrared and visible spectrum. The reference scan for transmission measurements is performed by simply taking a measurement through an empty sample chamber.

Data from the photodetectors 22 or 23 is amplified by an amplifier 24 and then converted from analog values to digital information by an analog converter 26. Then the digital data is transmitted to the computer 47 where the calculations are performed to convert the data to a useful form.

Absorbance, A is determined by the equation:

$$A = \log(1/T) \text{ or } A = \text{Log}(1/R)$$

The reflected or transmitted intensity from a sample or reference scan is determined for each 0.025 degree increment as determined by the optical encoder 19.

The determination of the center wavelength transmitted through the exit slit requires the solution of the following equation:

$$\text{Wavelength} = k(\text{sine } \theta + \phi)$$

where $\theta$ is the angular position of the grating incidence and k and $\phi$ are constants of the spectrophotometer. An equivalent equation which expresses the relationship of the angle of the grating to wavelength is:

$$\text{Wavelength} = K_1(\text{sine } \theta) + K_2(\text{cosine } \theta)$$

in which the coefficients $K_1$ and $K_2$ are constants of the spectrophotometer.

In accordance with the invention, a series of measurements is taken at every 0.025 degree angular increment over a multiplicity of cycles and average values are determined for the successive scans. The increments are determined by the encoder 19, and an average value at each increment is determined. The angle of the grating at each increment, $\theta$, is stored with the corresponding average value in the computer memory. The coefficients $K_1$ and $K_2$ are then determined by using the internal reference standard samples having known peaks of absorbance. By using the data for the known wavelengths that polystyrene exhibits peaks of absorbance and data which corresponds to the angle of the grating at which the peaks occur in the instrument while measuring the polystyrene, the coefficients $K_1$ and $K_2$ for the instrument are determined by linear regression and then corrected. After calculation, the coefficients are stored in the memory of the computer and are used in the subsequent measurement of an unknown sample to assign wavelengths to the measurements made on the unknown sample.

Four sets of coefficients $K_1$ and $K_2$ are initially determined for the instrument. One set of coefficients is to be used for reflectivity measurements in the near infrared range from 1100 nanometers to 2500 nanometers for reflectance measurements. A second set of coefficients $K_1$ and $K_2$ are also determined for the near infrared range for transmission measurements. A third set of coefficients $K_1$ and $K_2$ are determined for use in the visible light range for reflectance measurements and a fourth set of coefficients $K_1$ and $K_2$ are determined for use in the visible range for transmission measurements.

Figure 3:
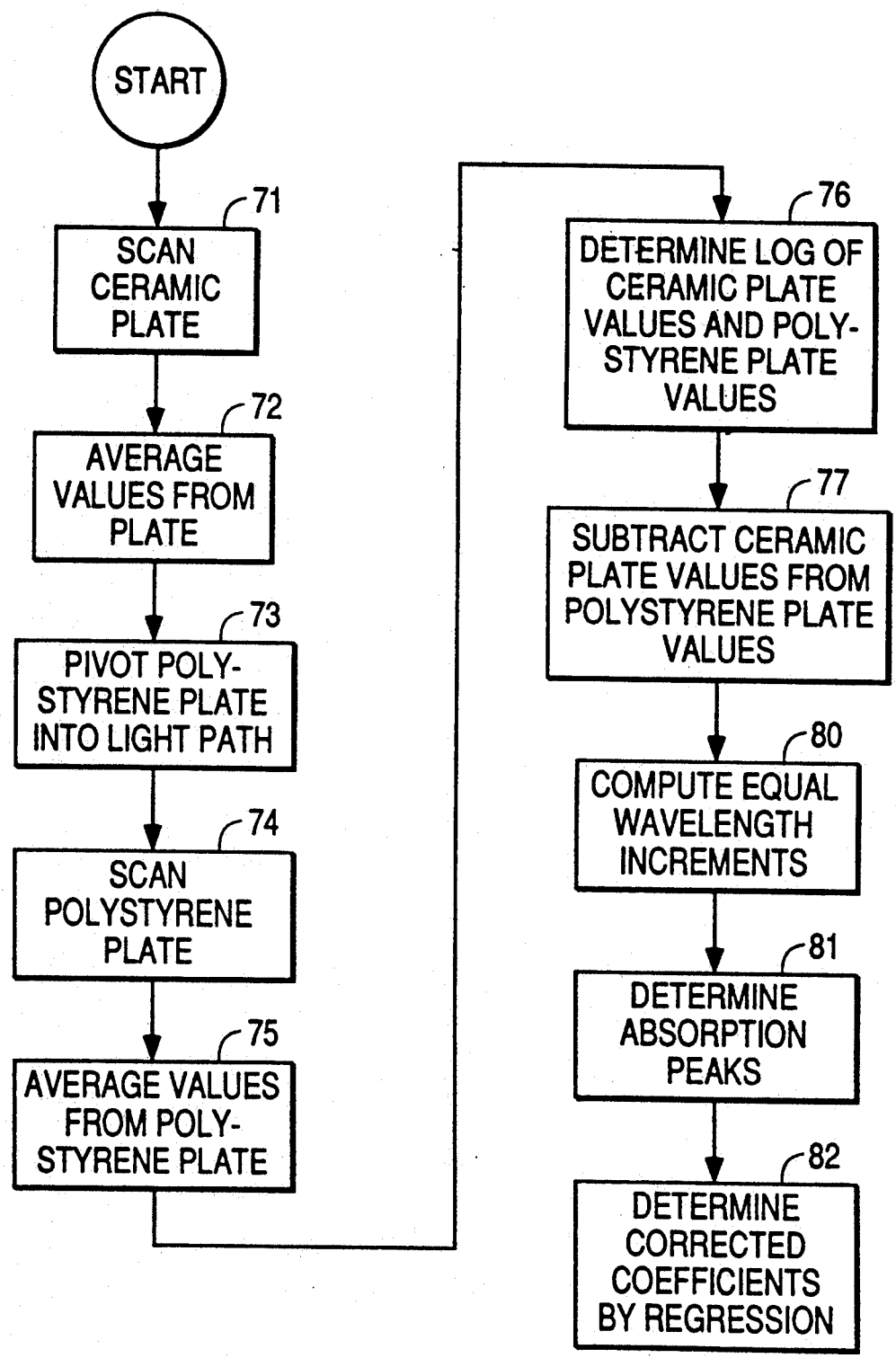
FIG. 3. is a flowchart illustrating a program employed in the computer of the of the system of the present invention to automatically recalibrate the instrument.
Figure 4:
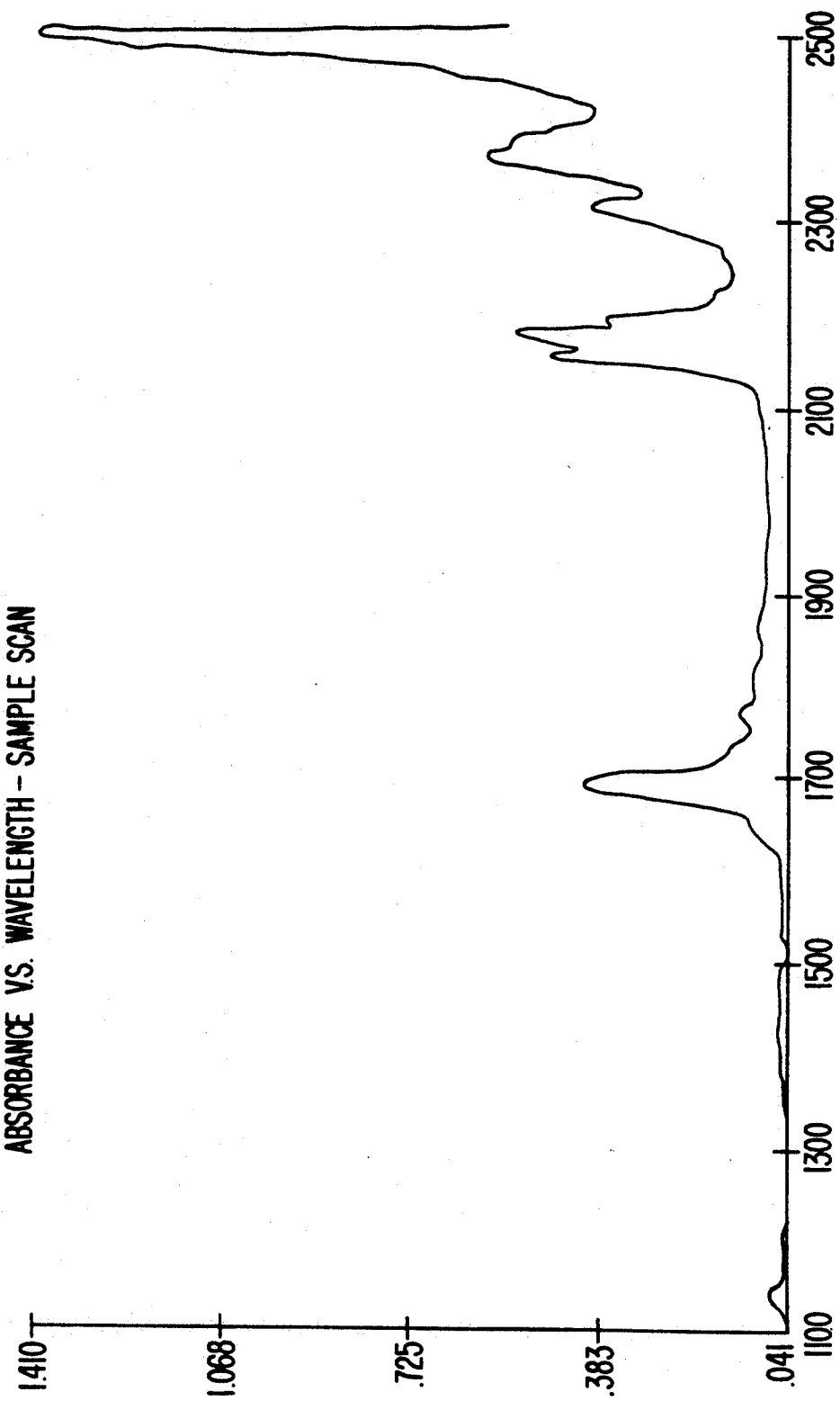
FIG. 4 is a graph which plots absorbance v. wavelength for a sample calibration scan of a polystyrene plate.

To initially determine the coefficients $K_1$ and $K_2$ for the near infrared range for reflectance measurements, the following procedure is carried out. First a reference scan with the Coors ceramic plate in position in the sample holder is carried out and with the absorbance standards pivoted out of the path of the light passing through the exit slit. The Coors plate is scanned several times in the near infrared red range between 1100 nanometers and 2500 nanometers and reflectance measurements from the Coors plate are taken at equal angular increments at 0.025 degrees throughout the near infrared spectrum. The reflectance measurements determined at each angular increment are averaged by the computer 47 and a set of average values is thus determined for the reference scan. Following the reference scan, the polystyrene plate is pivoted into the path of the light passing through the exit slit and the polystyrene plate and reflected by the Coors plate is scanned several times in the near infrared spectrum. Measurements are again taken at each 0.025 degree increment during each scan and the measurements are averaged by the computer 47. The scan through the polystyrene plate is called a calibration scan. The logarithm of the set of average reflection data taken during the reflectance scan and taken during the calibration scan through the polystyrene plate is determined and the logarithm data from the calibration scan is subtracted from the logarithm data obtained from the reference scan at each angular increment. This step yields a set of data at each 0.025 degree increments representing log 1/R which corresponds to the absorbance of the polystyrene plate. The absorbance of the polystyrene varies with wavelength in the near infrared range as shown in FIG. 3 and peaks of absorbance occur distributed throughout the near infrared spectrum. Absorbance peaks in polystyrene are known to occur precisely at 1143.63, 1681.12, 2166.75, and 2305.78 nanometers. Following the step of determining the set of absorbance data at each angular increment, the specific angles at which the above-identified peaks of absorbance occur is determined. This determination is carried out by the computer 57 using the method of peak determination described by Savitsky and Golay in an article entitled "Smoothing and Differentiation of Data by Simplified Least Squares Procedure" in the July, 1964 issue of *Analytical Chemistry*, pp. 1627-1638. The angle $\theta$ for each of the four peaks determined is then substituted in the equation, $\lambda = K_{1a} \sin\theta + K_{2a} \cos\theta$, along with the known wavelength to yield four simple equations with two unknowns, which are the coefficients $K_{1a}$ or $K_{2a}$. From these four equations, the values of $K_{1a}$ and $K_{2a}$ are calculated by regression. Then using the calculated values of $K_{1a}$ and $K_{2a}$, the set of absorbance data at equal angular increments is converted to a set of data at equal wavelength increments by simple interpolation. The peaks of absorbance are then again located in the equal wavelength increment data by the Savitsky and Golay method. Because of the transformation of the equal angular increment data to equal wavelength increment data, the positions of the absorbance peaks in the data will be slightly shifted. These differences are then substituted in the equation:

$$\delta\lambda = \delta K_1 \sin\theta + \delta K_2 \cos\theta$$

for each of the four peaks of absorbance. In the above equation $\delta\lambda$ is the difference between the known peak and the peak determined from the equal wavelength data. The values of $\delta K_1$ and $\delta K_2$ are determined from the four equations by regression. The initial values of $K_1$ and $K_2$ for the equal wavelength increment data are then calculated as follows:

$$K_1 = K_{1a} - \delta K_1 \text{ and } K_2 = K_{2a} - \delta K_2$$

The values of $K_1$ and $K_2$ are stored in the computer memory to be used in subsequent reflectance measurements of samples in the near infrared range.

A second set of coefficients $K_1$ and $K_2$ are computed for transmission measurements in a similar method differing only in that the Coors plate is not inserted in the sample holder and measurements during both the reference scan and the calibration scan are taken by the photodetector 23 so that the reference scan instruments are made of light transmitted through air and the calibration scan measurements are made directly of light transmitted through the polystyrene plate without reflection from the Coors plate.

The coefficients $K_1$ and $K_2$ are calculated for visual reflectance measurements in the same manner as described above for the reflectance measurements in the near infrared region, with the Coors ceramic plate 21 placed in the sample holder for the reference scan and the calibration scan, except that in pivoting the polystyrene plate into the path of the light passing through the exit slit during the calibration scan, the didymium plate is pivoted into the path so that the light passes through the didymium plate as well as through the polystyrene plate and the light passing through the exit slit is scanned through the visible spectrum from 400 nanometers to a little above 1141.01 nanometers. The polystyrene plate is virtually transparent in most of the visual range and does not affect the measurements made through the didymium plate. Didymium, like polystyrene, has known peaks of absorption which occur at 806.10 nanometers and 878.85 nanometers. A third peak in the absorption data occurring at 1141.01 nanometers is also used. This peak is actually caused primarily by the polystyrene and is caused by the same absorbance characteristic of the polystyrene that causes the absorbance peak at 1143.63 nanometers without the didymium plate. It is, however, shifted to 1141.01 nanometers because of the presence of the didymium plate through which the light is passing. Using the three peaks of absorption in the same manner as the four peaks in the near infrared region, the initial coefficients $K_1$ and $K_2$ are computed.

To determine the constants for the transmission data, the same process is repeated except without the Coors ceramic plate 21 placed in the sample holder and the transmission measurements are made by the photodetector 23.

In accordance with the present invention, the initially determined coefficients or constants $K_1$ and $K_2$ are corrected automatically before each measurement of an unknown sample in the manner invisible to the user. When the user of the instrument wants to take a measurement of the unknown sample, he is prompted by the instrument to conduct a reference scan. A reference scan must be conducted before each unknown sample measurement to be used in calculation of absorbance values from the unknown sample. If the measurement is to be a reflectance measurement, the user will see to it that the Coors plate is inserted into the sample holder. If the unknown sample is to be measured in the near infrared range, the user to initiate a reference scan will press an input key on the instrument calling for a reference scan in the near infrared range. In response to the actuation of the key calling for a reference scan, the instrument will perform a series of steps automatically as illustrated by the flowchart shown in FIG. 3 under the control of the computer 47 and in the program of the computer 47.

First, in step 71, the Coors ceramic plate is scanned throughout the infrared region a number of times with the absorbance standards pivoted out of the light passing through the exit slit. The photodetectors 22 detect the light reflected from the Coors plate and, after amplification and digitalization of the signal, the data is transmitted to computer 47, which stores the received data. Then in step 72, the computer determines an average reflectance value for the Coors plate for each angular increment. Next, in step 73, a polystyrene plate is automatically pivoted into the light path which exits housing 11 and a second scan is performed in step 74. This scan of light which passes through the polystyrene plate and reflected from the Coors plate is also performed a number of times and values for each angular increment are determined and stored by computer 47. After the scan is performed, the polystyrene plate is automatically pivoted out of the path of light and the computer 47 averages the values at each angle or increment received by the computer from the polystyrene plate in step 74. Next, the computer, in step 76, determines the logarithm of the average measurements from both the scan of the ceramic plate and from the scan of the polystyrene plate. The computer then, in step 77, subtracts the logarithms of the values determined for the polystyrene plate from the logarithm of values determined for the ceramic plate for each angular increment. The resulting data set will represent the absorbance of the polystyrene, log 1/R, at each angular increment. The above-described automatic steps described to this point are the same as those performed initially to calculate the initial values of $K_1$ and $K_2$. Following step 77, the computer, in step 80, uses the constants values $K_1$ and $K_2$ stored in the instrument for near infrared reflectance measurement, and the equation $\lambda = K_1 \sin \theta + K_2 \cos \theta$, to determine the absorbance values from the polystyrene at equal wavelength increments of two nanometers from the data at equal angular increments determined in step 77. The equal wavelength increment data are again determined by simple interpolation from the data at the equal angular increments. Then, in step 81, the computer 47 determines where in the equal wavelength data the peaks of absorption in the polystyrene occur by the Savitsky and Golay method. The computed wavelengths at which the peaks of absorption will probably be slightly different than the wavelengths at which the peaks actually occur because of drift and temperature change. If one or more of the differences in the wavelength are greater than preset tolerance limits, the operator is prompted to carry out a calibration scan to recalculate the values $K_1$ and $K_2$ as described above for the initial determination of these coefficients. If the wavelength differences are less than the preset tolerance limits, as would usually be the case, the computer enters into step 82 to compute corrected values of $K_1$ of $K_2$ from the equation $\Delta \lambda = \Delta K_1 \sine \theta + \Delta K_2 \cosine \theta$. In this equation, $\Delta \lambda$ is the difference between the wavelength determined in step 81 and the known wavelength at which the peak actually occurs. Since there are four peaks, there will be four equations and from these four equations, the values $\Delta K_1$ and $\Delta K_2$ are determined by regression. Then corrected coefficient values $K_1'$ and $K_2'$ are determined from the equation $K_1' = K_1 - \Delta K$ and $K_2' = K_2 - \Delta K_2$.

The corrected values $K_1'$ and $K_2'$ are then stored in the computer to replace the current values of $K_1$ and $K_2$ to be used in the subsequent measurement of the unknown sample, which measurement should be carried out immediately thereafter. In the measurement of the unknown sample, the unknown sample is placed in the sample holder and scanned in the manner described above. Measurements are taken at each 0.025 degree angular increment and the coefficients $K_1'$ and $K_2'$ are used to determine at what wavelengths these measurements are taken. Because the correction of the coefficients $K_1$ and $K_2$ is done automatically in response to the reference scan prompt prior to each unknown sample measurement, the coefficients $K_1$ and $K_2$ are corrected before each measurement and, thus, a high degree of accuracy for the unknown sample measurement is achieved.

For spectrophotometric analysis in the visible range, the same operational steps are carried out except the didymium filter is used in combination with the polystyrene plate and the scan is done in the visible range. The automatic coefficient correction method when using the didymium plate is essentially the same as recited above except that the didymium plate is pivoted into the path of the light passing through the exit slit during the calibration scan.

In the cases where it is desired to make transmission measurements, the reference and calibration scans are performed with the Coors plate removed. Referring back to FIG. 1, when the plate 21 is removed, the light path passes through an empty sample chamber and is detected by photodetector 23. Data from the detector 23 is amplified by amplifier 24 converted to a digital signal by converter 26 and transmitted to the computer 47. This data is also simultaneously related to an angular increment transmitted to the computer by shaft encoder 19. The same calibration steps are performed as shown in FIG. 3 using an empty chamber as the reference scan instead of the Coors plate.

In automatic systems in which the steps performing the reference scan and positioning the unknown sample, and scanning the unknown sample are all carried out automatically, the calibration scan and correction of the coefficients $K_1$ and $K_2$ are performed in the automatic process after the reference scan and before positioning the unknown sample.

While a preferred form of the invention has been disclosed here, it will be apparent to those skilled in the art that modifications and improvements can be made to the specific form herein disclosed without departing from the spirit and scope of the invention.

We claim:

1. In a spectrophotometer having an oscillating grating, an exit slit, said grating scanning the wavelength passing through said exit slit as said grating oscillates, a standard absorbance plate selectively positionable in the path of light passing through said exit slit, said absorbance plate exhibiting known peaks of absorbance at known wavelengths in a selected spectrum, means to detect the intensity of light passing through said exit slit and coming into contact with a sample, and means responsive to an input signal to oscillate said grating to perform a reference scan with said standard absorbance plate out of the path of the light passing through said slit, the improvement comprising calibrating means responsive to the input signal to automatically perform the following steps each time said reference scan is carried out:

(1) oscillating said grating to perform said reference scan with said standard absorbance plate out of the path of the light passing through said exit slit,
   (2) measuring the intensity of the light passing through said exit slit in step (1) at each angular increment of a set of angular increments of said grating distributed through said selected spectrum,
   (3) pivoting said standard absorbance plate into the path of light passing through said exit slit,
   (4) oscillating said grating to perform a calibration scan with said standard absorbance plate in the path of light passing through said exit slit,
   (5) measuring the intensity of the light passing through said exit slit in step (4) and optically contacting said absorbance plate at each of said angular increments,
   (6) determining the absorbance (log 1/R) of said standard absorbance plate at each of said angular increments from the measurements made in step (2) and (5),
   (7) determining the location of the peaks of absorbance occurring for said standard absorbance plate from the data determined in step (6),
   (8) computing corrected coefficients in an equation relating angular position of said grating to wavelength passing through said exit slit from the locations of the peaks determined in step (7) and the known wavelengths at which the peaks of absorbance occur in said standard absorbance plate, and
   (9) storing said corrected coefficients to be used by said instrument in measuring a transmittance or reflectance from an unknown sample.

2. A spectroscopic instrument as recited in claim 1, wherein said equation is $\lambda = K_1' \sin\theta + K_2' \cos\theta$, in which $\lambda$ is the wavelength passing through said exit slit, $\theta$ is the angular position of said grating and $K_1'$ and $K_2'$ are the corrected coefficients determined in step (8) by said automatic calibrating means.

3. An instrument as recited in claim 1, wherein said standard absorbance plate is a polystyrene plate and said spectrum is in the near infrared spectrum.

4. An instrument as recited in claim 1, wherein said standard absorbance plate is a light transmitting didymium plate and the spectrum is in the visible range.

5. An instrument as recited in claim 1, wherein said standard absorbance plate comprises a polystyrene plate and further comprising a didymium plate mounted on said polystyrene plate to eclipse a portion of polystyrene plate, said plates being selectively positionable to position said didymium plate in the path of light passing through said exit slit whereby the light passing through said exit slit passes through both said didymium plate and said polystyrene plate, or position said plates so that only said polystyrene plate is in the path of light passing through said exit slit, or so that both said didymium plate and said polystyrene plate are out of the path of light passing through said exit slit, said automatic calibrating means being operable to perform steps (1) through (8) to compute said corrected coefficients for the near infrared range with only said polystyrene plate pivoted into the path of light passing through said exit slit during step (3) and being operable to compute said corrected coefficients for the visible spectrum by performing steps (1) through (8) with said didymium plate pivoted into the path of light passing through said exit slit in step (3).

6. The instrument as recited in claim 5, wherein one of the peaks of absorbance for said calibrating means operating in said visible spectrum determined in step (7) is a peak of absorbance due to the light passing through said polystyrene plate.

7. A method for performing spectral analysis on a sample with a spectrometer having an oscillating grating, an exit slit wherein said grating scans the wavelength passing through said exit slit as said grating oscillates and means to detect the intensity of light passing through said exit slit and coming into contact with the sample, said method comprising performing the following steps (1) through (9) in sequence automatically each time an unknown sample is to be measured by said spectrometer:

(1) Oscillating said grating to perform a reference scan without a standard absorbance plate in the path of light passing through said exit slit,
   (2) Measuring the intensity of light passing through said exit slit in step (1) at each angular increment of a set of angular increments of said grating distributed through a selected spectrum,
   (3) Pivoting a standard absorbance plate into the path of light passing through the exit slit,
   (4) oscillating said grating to perform a calibration scan with said standard absorbance plate in the path of light passing through said exit slit,
   (5) measuring the intensity of the light passing through said exit slit in step (4) and optically contacting said absorbance plate at each of said angular increments, (6) determining the absorbance (log 1/R) of said standard absorbance plate at each of said angular increments from the measurements made in step (2) and (5), (7) determining the location of the peaks of absorbance occurring for said standard absorbance plate from the data determined in step (6), (8) computing corrected coefficients in an equation relating angular position of said granting to wavelength passing through said exit slit from the locations of the peaks determined in step (7) and the known wavelengths at which the peaks of absorbance occur in said standard absorbance plate, and (9) storing said corrected coefficients to be used by said instrument in measuring a transmittance or reflectance from an unknown sample,

(10) then positioning said unknown sample to be measured in the path of light passing through said exit slit,

(11) then oscillating said grating to perform a scan of said unknown sample, measuring the intensity of light passing through said exit slit and optically contacting said sample at each of said angular increments, and using the coefficients stored in step (9) to determine the wavelength at which the measurements from the sample are taken.

* * * * *